United States Patent [19]

Trainer

[11] Patent Number: 6,164,817
[45] Date of Patent: Dec. 26, 2000

[54] FIBER OPTIC HYGROMETER APPARATUS AND METHOD

[75] Inventor: Michael N. Trainer, Telford, Pa.

[73] Assignee: Honeywell, Inc., Morristown, N.J.

[21] Appl. No.: 09/145,072

[22] Filed: Sep. 1, 1998

[51] Int. Cl.[7] .................................................. G01N 25/02
[52] U.S. Cl. .......................... 374/19; 385/12; 73/335.01; 374/20; 374/18
[58] Field of Search .................................. 374/17, 18, 19, 374/20, 28; 385/12, 31; 73/335.01

[56] References Cited

U.S. PATENT DOCUMENTS

| | | | |
|---|---|---|---|
| 3,050,982 | 8/1962 | Vollmer et al. | 374/17 |
| 4,894,532 | 1/1990 | Peterson et al. | 250/226 |
| 5,178,462 | 1/1993 | Lehto | 374/17 |
| 5,747,348 | 5/1998 | Jaduszliwer et al. | 385/12 |
| 5,779,365 | 7/1998 | Takaki | 374/161 |
| 5,920,010 | 7/1999 | Derevyagin et al. | 73/335.01 |
| 5,982,959 | 11/1999 | Hopenfeld | 385/12 |
| 5,995,686 | 11/1999 | Hamburger et al. | 385/12 |

FOREIGN PATENT DOCUMENTS 8908273  9/1989  WIPO ....................... 385/12

*Primary Examiner*—Diego Gutierrez
*Assistant Examiner*—Lydia M. De Jesús
*Attorney, Agent, or Firm*—Anthony Miologos

[57] ABSTRACT

A fiber optic hygrometer apparatus and method for sensing and measuring the dew point of an atmosphere is disclosed that includes a controller for controlling the operation of the apparatus and a first optical fiber for transmitting light energy from a source of light energy to an optical core extending into the atmosphere being monitored. The optical core includes an end that is prepared as a reflecting surface, allowing the light energy reaching the optical core to be internally reflected back toward the source. A second optical fiber captures the light energy internally reflected from the optical core and conveys the captured light energy to a light energy detector. The light energy detector is arranged to output signals to the controller representing the magnitude of the light energy captured. A cooling device and a temperature-sensing device operationally connected to the controller are attached to the optical core. The cooling device is disposed to cool the optical core to a temperature below the ambient temperature of the atmosphere and cause water vapor that may be contained in the atmosphere to condense on the optical core, forming an evanescent region in the area of the condensate and thereby decreasing the magnitude of light energy captured by the second optical fiber. The light energy detector outputs signals to the controller representative of the decreased magnitude of light energy captured, causing the controller to read the temperature of the optical core sensed by the temperature device.

16 Claims, 2 Drawing Sheets

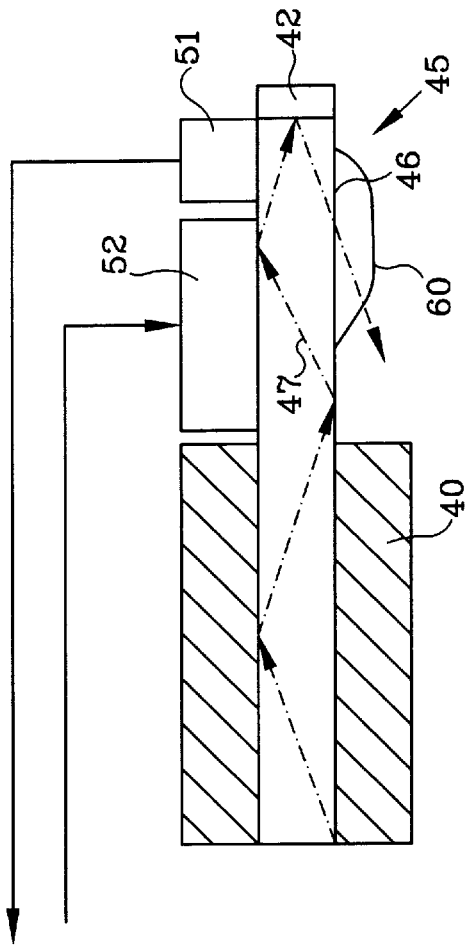
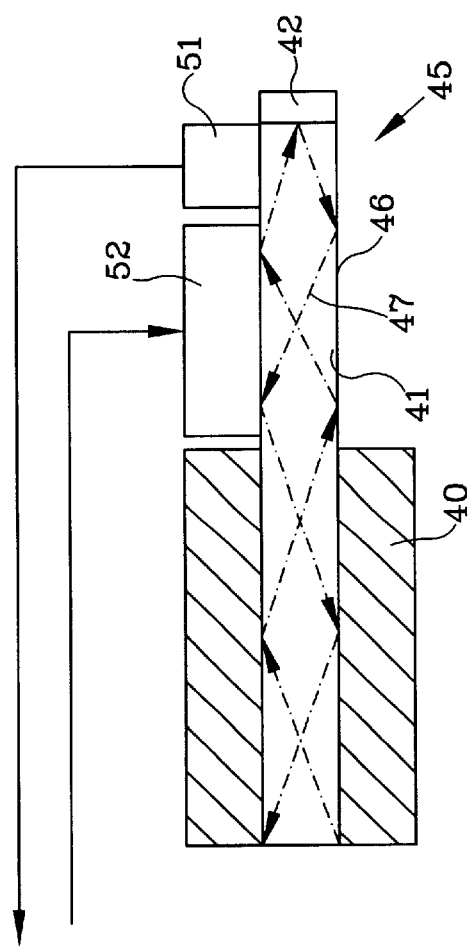

FIBER OPTIC HYGROMETER APPARATUS AND METHOD

CROSS-REFERENCE TO RELATED APPLICATIONS

This present application is related to applicant's patent application Ser. No. 09/145,068, now U.S. Pat. No. 6,084,665, entitled, "Optical Sensor for Detecting the Dew Point of an Atmosphere", filed on an even date herewith and assigned to a common assignee with the present invention.

BACKGROUND OF THE INVENTION

1. Field of the Invention

The present invention relates generally to hygrometers and, more specifically, to a fiber optic apparatus and method for sensing the dew point of an atmosphere in a process environment.

2. Discussion of the Related Art

Many methods of sensing the humidity levels present in a gaseous atmosphere are based upon inferring the moisture content of a sample from an output of a moisture-sensitive transducer. Such methods may be subject to such inherent limitations as a non-linear variation of the output parameter with humidity, drift, temperature sensitivity, hysteresis and aging. The limitation of temperature relates to the fact that the water-holding capacity of a gas varies with temperature so that only a relative humidity rather than an absolute measurement is provided. Relative humidity can be related to absolute humidity by using known conversion algorithms, such as the Goff-Gratch equation. However, this algorithmic solution can not be conveniently embodied in a linear circuit.

One method presently known and used extensively in industry for providing absolute humidity readings is to use chilled mirror hygrometers that provide an indication of dew point or frost point, each of which is a primary measurement of moisture content. The dew point is the temperature at which the partial pressure of a condensate on a surface equals the water vapor partial pressure in a gas. Similarly, frost point is the saturation temperature to which the gas temperature must be cooled at constant pressure so that it will be saturated in respect to ice. Saturation vapor pressure is a unique function of temperature. Therefore, determining the temperature at which water vapor begins to condense on a cool surface is equivalent to a measurement of its partial pressure.

Chilled mirror hygrometers use cooled mirrors as the surface where condensation takes place. Using electro-optic circuitry, a precise determination of the formation of either dew or frost is made. A temperature transducer, such as a platinum resistance transducer, is used to provide the signal indicating the output information.

One of the limitations of using such chilled mirror hygrometers in industrial applications is the inability of the electro-optic elements to differentiate between dew or frost deposits and dirt or soot deposits that may coat the mirror by particulate by-products of the process being measured. Since dew, as well as contaminants such as dirt deposits, will be measured by the included photosensors as a loss of reflected light, a differentiation between the dew and contaminant conditions must be made to ensure the accuracy of the hygrometer. Prior art responses in dealing with this type of contamination included cleaning procedures that are performed periodically or on an event-dependent basis. Another method employs compensation procedures in the hygrometers operation that "balance" the system. This is done by, in essence, performing a calibration operation to "null" variations in the optic sensitivity scheme due to the contaminant deposited on the mirror. This is accomplished by raising the temperature of the mirror to a temperature higher than the dew point to ensure a dry mirror so that the loss in reflectivity due to the contaminant alone may be measured. Adjustments are than made to the optical sensing circuitry to compensate for any differences in respect to the original calibration values.

Both these methods require taking the hygrometer "off-line", thereby losing the ability to monitor the process while the cleaning or compensation procedures are being performed. Additionally, as the contaminant deposits coating the mirror become more expansive, the compensation procedure explained above requires it be performed more frequently, increasing the time and frequency which the hygrometer must be off-line.

BRIEF SUMMARY OF THE INVENTION

In accordance to the present invention, there is provided an apparatus for sensing and measuring the dew point of an atmosphere. The apparatus includes a controller for controlling the operation of the apparatus and a first optical fiber for transmitting light energy from a source of light energy to an optical core that extends into, and is exposed to, the atmosphere of a process environment being monitored. The optical core includes an end that is prepared as a reflecting surface, allowing the light energy reaching the optical core to be internally reflected back down toward the source.

A second optical fiber is optically connected to the first optical fiber and is arranged to capture the light energy internally reflected from the optical core. The second optical fiber conveys the captured light energy to a light energy detector. The light energy detector is arranged to output signals to the controller representing the magnitude of the light energy captured.

A cooling device is attached to the optical core and is operatively connected to the controller. The cooling device is arranged to cool the optical core to a temperature below the ambient temperature of the atmosphere to cause water vapor that may be contained in the atmosphere to condense on the optical core. The apparatus further includes a temperature-sensing device that is operatively connected to the controller that measures the temperature of the optical core.

Responsive to the deposition of condensate on the optical core an evanescent region is formed in the area of the condensate, decreasing the magnitude of light energy internally reflected in the optical core and captured by the second optical fiber. The light energy detector outputs signals to the controller representative of the decreased magnitude of light energy captured, causing the controller to read the temperature of the optical core sensed by the temperature device and thereby establishing the dew point of the atmosphere.

The present invention can also be effectively used to detect and signal the presence of a liquid. As a liquid detector, the apparatus has a first optical fiber transmitting light energy from a source of light energy to an optical core extending into an area where the presence of a liquid is to be sensed. The optical core includes an end prepared as a reflecting surface for reflecting back into the optical core the light energy that strikes the reflecting surface.

A second optical fiber is optically connected to the first optical fiber that couples and transmits the light energy reflected from the optical core to a light energy detector. The light energy detector is arranged to output signals representative of the magnitude of light energy detected. Responsive to liquid contacting the optical core, an evanescent region is formed in the area of the liquid contact, decreasing the magnitude of the light energy coupled to the second optical fiber. The light energy detector outputs signals representative of the decreased magnitude of light energy, thereby signaling the presence of a liquid.

It is, therefore, an object of the present invention to provide a hygrometer that is not affected by contaminants found in the process environment.

It is also an object of the present invention to provide a simple optical fiber apparatus that can continuously and effectively monitor the dew point of an atmosphere of a process environment without the need of going "off-line" to clean, compensate or balance the operation of the apparatus.

It is also a further object of the present invention to provide an apparatus and method that is less technically complex and, therefore, more operationally reliable than apparatus and methods currently known.

BRIEF DESCRIPTION OF THE SEVERAL VIEWS OF THE DRAWINGS

Other objects, features, and advantages of the present invention will be apparent from the following description of a preferred embodiment thereof, taken in conjunction with the sheets of drawings, in which:

FIG. 2 is a detailed sectional view of the fiber end of FIG. 1, showing the conduct of light energy when it strikes the glass-air interface of the unclad fiber core.

FIG. 3 is a detailed sectional view of the fiber end of FIG. 1, showing the conduct of light energy when the glass-air interface of the unclad fiber core is modified by a liquid deposit.

DETAILED DESCRIPTION OF THE INVENTION

Figure 1:
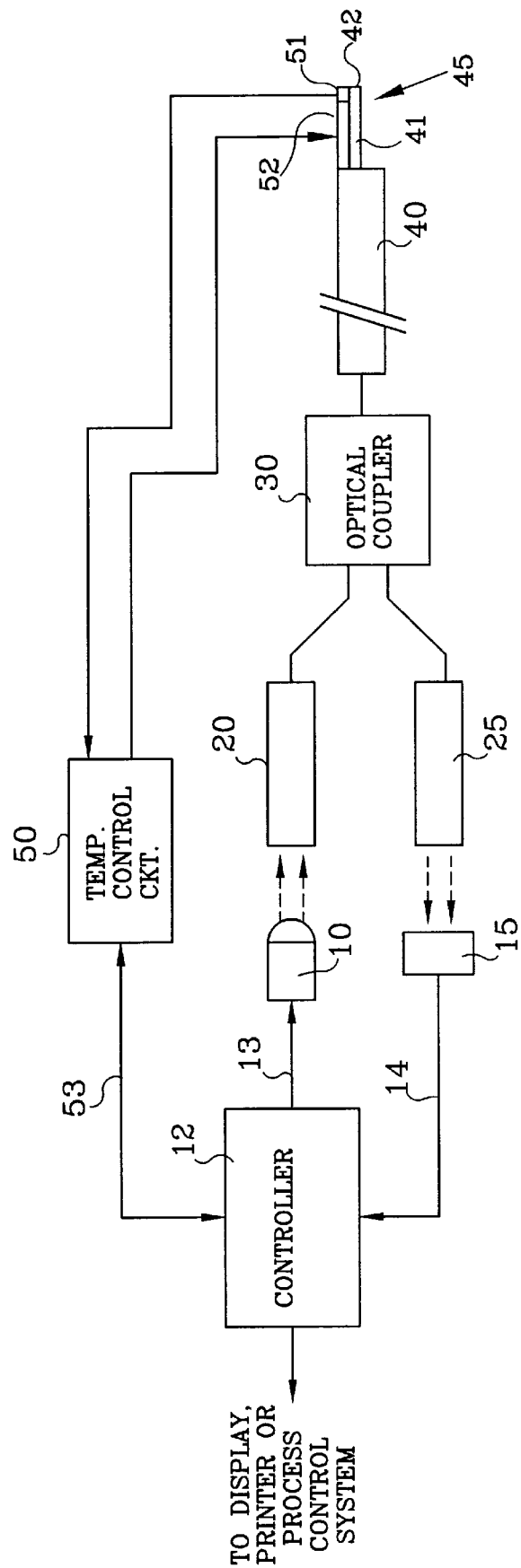
FIG. 1 is a diagram of the fiber optic apparatus in accordance to the present invention.

The sensor of the present invention contemplates the use of an optical fiber that consists of transparent material, such as glass or plastic. Most glass optical fiber is fused silica and most plastic fiber is polymethylmethacrylate (PMMA). All optical fiber structure consists of a core of glass or plastic jacketed with a cladding having a lower refractive index than the core. The fiber structure guides light by the process of total internal reflection (TIR). Optical fibers fall into two basic types: single mode or multimode. In single mode fibers the core is very small, 5 to 10 microns in diameter, for instance. Multimode fibers have cores of 50 to several thousand microns and very small cladding thicknesses (in order of tens of microns). Single mode fibers, however, typically have large cladding (usually more than 50 microns), making the fiber diameter generally 125 microns. The purpose of the large cladding in single mode fiber is to protect and contain the evanescent field of the single mode fiber which extends into the cladding for several microns and can contain more than 10 percent of the optical energy normally thought of as traveling only through the core. Another importance of this larger diameter cladding is so that the fibers are not too small for handling.

In a fiber having its cladding stripped away, the majority of the light energy striking the glass-air interface is internally reflected. Just on the other side of this interface, where the reflection occurs, the light exits for a short distance in the physical form of an evanescent field. If water or other liquid condensate is attached to the exterior of the fiber core at this locality, the index of refraction is changed, causing light energy to be drawn in and absorbed by the condensate. This phenomenon is optically detectable by a reduction of the light level internally reflected within the fiber. The present invention uses this evanescent phenomenon as a means of detecting or sensing the dew point or moisture content found in the atmosphere of a process environment.

Turning now to FIG. 1, the major components of the present invention are illustrated. A source of light energy 10 is optically coupled to a first optical fiber segment 20 that in turn is optically connected to an optical fiber coupler 30. The optical fiber coupler 30 is connected to an optical fiber conductor 40, which extends out to the process environment whose atmosphere is to be measured for moisture content. The present embodiment shows the use of a single mode optical fiber; however, it will be well understood by those skilled in the art that a multimode fiber could also be used to practice the present invention. The optical fiber coupler 30 is further connected to a second optical fiber segment 25 with the second optical fiber segment 25 optically connected to a light detector device 15. Both the light source 10 and the light detector device 15 are electrically connected to a controller 12 by signal leads 13 and 14, respectively. The controller 12 is arranged to provide signals to enable and disable the light source 10 and to receive and process the electrical signals from the light detector device 15 that represent the intensity or magnitude of the light received by light detector device 15. The controller 12 is further connected to a temperature control circuit 50 via signal path 53. The end 45 of the optical fiber conductor 40 extends into the process environment and has its cladding removed, thereby exposing the core 41 to the process environment.

As can be seen in FIG. 2, the tip 46 of the core 41 is cleaved, polished and coated with reflecting material. A temperature sensor or thermocouple 51 is electrically connected to the temperature control circuit 50 and is attached to core 41. Similarly, a thermoelectric cooler 52 is also attached to core 41 and is controlled by the temperature control circuit 50. Upon command from the controller 12, the temperature control circuit 50 activates the thermoelectric cooler 52 to cool the exposed core 41, and the temperature sensor 51 is used to measure the temperature of the exposed core 41.

With renewed reference to FIGS. 1 and 2, the method of operation of the present invention will now be described. Upon a signal from the controller 12, the light source 10 is enabled, coupling the light energy radiating from the light source into the first fiber optic segment 20. The light energy is internally reflected through the optical fiber coupler 30 to the optical fiber conductor 40. The light energy is carried by the optical fiber conductor 40 to the exposed core 41. At core 41 the light energy is reflected off the core tip 42 and is internally reflected back through the optical fiber conductor 40, optical fiber coupler 30 and the second optical fiber segment 25 to the light detector device 15. The light detector 15 produces a signal to the controller 12 representing the amount or intensity of light that is returned through the optical fiber coupler 30 from the tip 42 of the fiber optic core 41. In this non-cooled state, the majority of the light reflecting off of tip 42 and striking the unclad glass-air interface 46 is internally reflected into the optical fiber conductor 40, as illustrated by line 47.

As can be seen in FIG. 3, upon command from the controller 12, the temperature control circuit 50 sends a signal to the thermoelectric cooler 52, whereby the cooler 52 begins to cool core 41. When core 41 cools sufficiently, any water vapor present within the process environment that is being measured will condense and form deposits of water 60 on core 41. The water deposits 60 become attached to the core, modifying the index of refraction of the glass-air interface 46 to a glass-water interface. The evanescent phenomenon causes the internally reflected light energy to be redirected from the core 41 and to be diverted into and absorbed by the condensate. Since light energy is now spilling from the locality of the condensate, the light detector 15 receives and detects a decreased magnitude of light energy intensity. Upon the detection of this decreased light level, the controller 12 signals the temperature control circuit 50 to read the temperature of core 41 via temperature sensor 51, thereby establishing the dew point of the atmosphere of the process environment. The temperature just read is passed from the temperature control circuit 50 to the controller 12, where the controller 12 outputs a signal to a display device, printer or process control system (not shown). Alternatively, the signal output by the controller 12 can be in the form of an alarm signal that can signal a condition requiring immediate attention.

In situations when the ambient temperature of the atmosphere of the process environment is lower than the atmosphere's dew point, the thermoelectric cooler 52 can be used to heat the core 41 well above the dew point to evaporate any water or liquid deposits 60 that may be attached to core 41. The cooler 52 is then commanded to cool core 41 toward the dew point and the dew point temperature ascertained in accordance to the method of the present invention described above.

It will be well understood by those skilled in the art that the present invention can also be effectively used to detect and sense the presence of any liquid or a liquid level. In the detection of a liquid, or of a liquid level, the temperature control circuit 50, thermoelectric cooler 52 and temperature sensor 51 would not be required. Any liquid coating the unclad core 41 would cause the light energy to be directed from core 41 via the evanescent phenomenon explained above. Upon detection by the light detector 15 of a decreased light intensity level, a signal can be output by the controller 12 to announce the presence of a liquid or the level of a liquid, for example, in a vessel or container. The present invention provides a simple and effective means for the detection of the water vapor or dew point of a process environment and is insensitive to dust, soot or other contaminants that may collect on the surface of the unclad fiber due to the contaminants that may be present or inherent within the process environment.

The present invention has been described with particular reference to the preferred embodiments thereof. It will be obvious that various changes and modifications can be made therein without departing from the spirit and scope of the invention as defined in the appended claims.

What is claimed is:

1. An apparatus for measuring the dew point of an atmosphere comprising:

means for controlling the operation of said apparatus;

first means for transmitting light energy from a source of light energy to an optical core extending into said atmosphere, said optical core including an end prepared as a reflecting surface;

second means for transmitting light energy connected to said first means for transmitting light energy, coupling the light energy reflected from said reflecting surface to a light energy detector, said light energy detector arranged to output signals to said means for controlling, which represent the magnitude of said light energy detected;

means for cooling said optical core operatively connected to said means for controlling arranged to cool said optical core to a temperature below the ambient temperature of said atmosphere to cause water vapor that may be contained in said atmosphere to condense on said optical core; and means for measuring the temperature of the optical core operatively connected to said means for controlling and responsive to the deposition of condensate on said optical core, an evanescent region is formed in the area of said condensate, decreasing the magnitude of light energy coupled to said second means for transmitting light energy, wherein said light energy detector outputs to said means for controlling output signals representative of said decreased magnitude of light energy, causing said means for controlling to read the temperature of said optical core and establish the dew point of said atmosphere.

2. The apparatus in accordance to claim 1 wherein said first means for transmitting light energy is a first optical fiber comprised of a light transmitting core surrounded by a cladding, said first optical fiber including a first end having its core optically coupled to said light source and a second end having said cladding surrounding said core removed, forming said optical core extending into said atmosphere.

3. The apparatus in accordance to claim 1 wherein said means for cooling is a thermoelectric cooler attached to said optical core.

4. The apparatus in accordance to claim 2 wherein said second means for transmitting light energy is a second optical fiber comprised of a light-transmitting core surrounded by a cladding, said second optical fiber including a first end having its core connected to the first optical fiber core at an optical junction, said optical junction arranged to capture the light energy internally reflected through said first optical fiber from said optical core, and said second optical fiber further including a second end optically connected to said light energy detector, whereby said light energy captured by said optical junction is transmitted to said light energy detector.

5. The apparatus in accordance to claim 4 wherein said optical junction is a fiber optic coupler.

6. The apparatus in accordance to claim 1 wherein said cooling means is operatively connected to said means for controlling through a temperature control circuit, and said temperature control circuit controls the enabling and disabling of said cooling means in accordance to control signals from said means for controlling.

7. The apparatus in accordance to claim 6 wherein said means for measuring the temperature of said optical core is a temperature sensing device attached to said optical core and arranged to output signals representing the temperature of said optical core to said temperature control circuit, whereby said controlling means reads the temperature of said optical core from said temperature control circuit in response to said light energy detector output sign.

8. The apparatus in accordance to claim 6 wherein said means for measuring the temperature of said optical core is a thermocouple device attached to said optical core arranged to produce a voltage representing the temperature of said optical core to said temperature control circuit, whereby said controlling means reads the temperature of said optical core from said temperature control circuit in response to said light energy detector output signals.

9. An apparatus for measuring the dew point of an atmosphere comprising:

a controller for controlling the operation of said apparatus;

a first optical fiber having a core and first and second ends, said first end optically connected to a source of light energy coupling said light energy into said core and said second end having an exposed core extending into said atmosphere, said exposed core further including a tip end prepared as a reflecting surface for returning said light energy striking said reflecting surface into said core;

a second optical fiber having a core and first and second ends, said core of said first end optically connected to said first optical fiber core between said first optical fiber first and second ends arranged to form an optical junction thereat for capturing the light energy reflected from said tip end into said second optical fiber core and arranged to convey said light energy captured to a light detector optically connected to said second optical fiber second end, said light detector arranged to receive and output signals to said controller representative of the magnitude of said light energy captured;

a cooling device under control of said controller arranged to cool said exposed core to a temperature below the ambient temperature of the atmosphere, to cause water vapor contained in said atmosphere to condense on said exposed core; and a temperature sensing device for measuring the temperature of said exposed core operatively connected to said controller and responsive to the deposition of condensate on said exposed core an evanescent region is formed in the area of said condensate, decreasing the magnitude of light energy coupled to said second optical fiber, wherein said light detector outputs a signal to said controller representative of said decreased magnitude of light energy, causing said controller to read the temperature of said exposed core measured by said temperature sensor to establish the dew point of said atmosphere.

10. The apparatus in accordance to claim 9 wherein said optical junction is a fiber optic coupler.

11. The apparatus in accordance to claim 9 wherein said cooling device is a thermoelectric cooler attached to said exposed core.

12. The apparatus in accordance to claim 9 wherein said temperature sensing device is a temperature sensor attached to said exposed core arranged to produce output signals representing the temperature of said optical core.

13. The apparatus in accordance to claim 9 wherein said temperature sensing device is a thermocouple attached to said optical core arranged to produce a voltage representing the temperature of said optical core.

14. The apparatus in accordance to claim 9 wherein said tip end is prepared as a reflecting surface by cleaving the exposed core and polishing and coating the cleaved end with a reflective material.

15. A method for measuring the dew point of an atmosphere comprising the steps of:

transmitting light energy from a light energy source to an optical core extending into said atmosphere, said optical core including a reflecting surface reflecting said light energy striking said surface back into said optical core;

cooling said optical core to a temperature below the ambient temperature of the atmosphere to cause condensation to be deposited on said optical core, forming an evanescent region in the area of said condensate;

capturing the light energy contained within said optical core and transmitting the captured light energy to a light detector; and reading the temperature of said optical core responsive to a decreased magnitude of light energy detected by said light detector thereby establishing the dew point of said atmosphere.

16. An apparatus for measuring the dew point of an atmosphere comprising:

means for directing light energy to an optical core extending into said atmosphere;

means for cooling said optical core to a temperature below the ambient temperature of said atmosphere to cause water vapor that may be contained in said atmosphere to condense on said optical core, forming an evanescent region in the area of said condensate;

means for internally reflecting the light energy contained in said optical core to a light energy detector, said light energy detector arranged to output signals representative of the magnitude of said light energy detected; and means for measuring the temperature of said optical core arranged to receive said output signals and to read the temperature of said optical core responsive to a decreased magnitude of light energy detected by said light energy detector thereby establishing the dew point of said atmosphere.

* * * * *